(12) United States Patent
Sztor et al.

(10) Patent No.: US 8,716,180 B2
(45) Date of Patent: *May 6, 2014

(54) METHOD OF REDUCING MYCOTOXIN CONTAMINATION OF THE HARVEST

(75) Inventors: Edmond Sztor, Villepreux (FR); Pascal Poels, St Cyr l'Ecole (FR); Michael Oostendorp, Basel (CH); Franz Brandl, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 496 days.

This patent is subject to a terminal disclaimer.

(21) Appl. No.: 11/994,206

(22) PCT Filed: Jun. 28, 2006

(86) PCT No.: PCT/EP2006/006260
§ 371 (c)(1),
(2), (4) Date: Mar. 24, 2010

(87) PCT Pub. No.: WO2007/003320
PCT Pub. Date: Jan. 11, 2007

(65) Prior Publication Data
US 2010/0173773 A1    Jul. 8, 2010

(30) Foreign Application Priority Data

Jun. 30, 2005 (EP) .................................. 05291424

(51) Int. Cl.
| | | |
|---|---|---|
| *A01N 25/00* | (2006.01) | |
| *A01N 3/02* | (2006.01) | |
| *A01N 43/72* | (2006.01) | |
| *A01N 43/36* | (2006.01) | |
| *A01N 43/02* | (2006.01) | |
| *A01N 47/28* | (2006.01) | |
| *A01N 37/12* | (2006.01) | |
| *A01N 37/44* | (2006.01) | |
| *A61K 31/41* | (2006.01) | |
| *A61K 31/335* | (2006.01) | |
| *A61K 31/195* | (2006.01) | |
| *C07D 239/42* | (2006.01) | |
| *C07D 401/04* | (2006.01) | |

(52) U.S. Cl.
USPC ........... 504/100; 504/113; 504/118; 504/129; 504/131; 504/132; 504/138; 504/140; 504/148; 504/189; 504/209; 514/229.2; 514/256; 514/383; 514/422; 514/452; 514/467; 514/563

(58) Field of Classification Search
USPC ......... 504/100, 113, 118, 129, 131, 132, 138, 504/140, 148, 189, 209; 514/229.2, 256, 514/383, 467, 422, 452, 563
See application file for complete search history.

(56) References Cited

U.S. PATENT DOCUMENTS

2009/0270471 A1 * 10/2009 Buschhaus .................... 514/383

FOREIGN PATENT DOCUMENTS

| DE | 2139755 A1 * | 2/1973 | ............ A01N 47/18 |
|---|---|---|---|
| DE | 2139755 A1 * | 8/1973 | ............ A01N 21/00 |
| DE | 2139755 A1 * | 9/1992 | ............ A01N 63/02 |
| DE | 4205196 A * | 9/1992 | ............ A01N 63/00 |
| DE | 4205196 A1 * | 9/1992 | ............ A01N 63/00 |
| DE | 4205196 A1 | 9/1992 | |
| WO | 2002/019827 A | 3/2002 | |
| WO | 2004/024865 A | 3/2004 | |
| WO | WO2004024865 A2 * | 3/2004 | |

OTHER PUBLICATIONS

C.L. Maurya, "Effect of seed treatment and storage period on the longevity of hybrid rice seed," 2005, Plant Archives, 5(2): 601-604.*
C. L. Maurya, Effect of seed treatment and storage period on the longevity of hybrid rice seed (*Oryza sativa* L.), 2005, Plant Archives, vol. 5, No. 2, pp. 601-604.*
Padule et al., "Efficacy of fungicides for increasing storability of grain moulds infected seed of sorghum hybrid," 1999, Seed Research, 27(1): 95-99.*
C.L. Maurya, "Effect of seed treatment and storage period on the longevity of hybrid rice seed," 2005, Plant Archives, 5(2):601-604.*

* cited by examiner

*Primary Examiner* — Jane C Osswecki
(74) *Attorney, Agent, or Firm* — R. Kody Jones

(57) ABSTRACT

The present invention provides a method of reducing mycotoxin contamination of a plant and/or harvested plant material, said method comprising treating plant propagation material with one or more fungicides, germinating or growing said plant propagation material to produce a plant, and harvesting plant material from said plant.

13 Claims, No Drawings

METHOD OF REDUCING MYCOTOXIN CONTAMINATION OF THE HARVEST

This application is a National Stage Entry under 35 USC §371 of International application serial number PCT/EP2006/006260, filed on Jun. 28, 2006, which claims priority to EP 05291424.9, filed on Jun. 30, 2005, the contents of which are incorporated herein by reference.

The present application relates to methods for the reduction of mycotoxin contamination of plant and/or harvested plant material, which involves chemical fungicide treatment of plant propagation material.

Numerous fungi are serious pests of economically important agricultural crops. Further, crop contamination by fungal toxins is a major problem for agriculture throughout the world. Mycotoxins, such as fumonisins, zearalenones, and trichothecenes, are toxic fungal metabolites, often found in agricultural products that are characterized by their ability to cause health problems for vertebrates.

Trichothecenes are sesquiterpene epoxide mycotoxins produced by species of *Fusarium, Trichothecium*, and *Myrothecium* that act as potent inhibitors of eukaryotic protein synthesis.

Examples of trichothecene mycotoxins include T-2 toxin, HT-2 toxin, isotrichodermol, DAS, 3-deacetylcalonectrin, 3,15-dideacetylcalonectrin, scirpentriol, neosolaniol; 15-acetyldeoxynivalenol, nivalenol, 4-acetylnivalenol (fusarenone-X), 4,15-diacetylnivalenol, 4,7,15-acetylnivalenol, and deoxynivalenol (hereinafter "DON") and their various acetylated derivatives.

Fumonisins are toxins produced by *Fusarium* species that grow on several agricultural commodities, mainly corn, in the field or during storage. The disease, Fusarium kernel rot of corn, is caused by *Fusarium verticillioides* and *F. proliferatum*, common producers of fumonisin. More than ten chemical forms of fumonisins have been isolated, of which fumonisin $B_1$ is the most prevalent in contaminated corn and is believed to be the most toxic.

*Fusarium* species that produce mycotoxins, such as fumonisins and trichothecenes, include *F. acuminatum, F. crookwellense, F., verticillioides, F. culmorum, F. avenaceum, F. equiseti, F. moniliforme, F. graminearum (Gibberella zeae), F. lateritium, F. poae, F. sambucinum (G. pulicaris), F. proliferatum, F. subglutinans* and *F. sporotrichioides*.

Both acute and chronic mycotoxicoses in farm animals and in humans have been associated with consumption of wheat, rye, barley, oats, rice and maize contaminated with *Fusarium* species that produce trichothecene mycotoxins. Experiments with chemically pure trichothecenes at low dosage levels have reproduced many of the features observed in moldy-grain toxicoses in animals, including anemia and immunosuppression, haemorrage, emesis and feed refusal. Historical and epidemiological data from human populations indicate an association between certain disease epidemics and consumption of grain infected with *Fusarium* species that produce trichothecenes. In particular, outbreaks of a fatal disease known as alimentary toxic aleukia, which has occurred in Russia since the nineteenth century, have been associated with consumption of over-wintered grains contaminated with *Fusarium* species that produce the trichothecene T-2 toxin. In Japan, outbreaks of a similar disease called akakabi-byo or red mold disease have been associated with grain infected with *Fusarium* species that produce the trichothecene, DON. Trichothecenes were detected in the toxic grain samples responsible for recent human disease outbreaks in India and Japan. There exists, therefore, a need for agricultural methods for preventing, and crops having reduced levels of, mycotoxin contamination.

Further, mycotoxin-producing *Fusarium* species are destructive pathogens and attack a wide range of plant species. The acute phytotoxicity of mycotoxins and their occurrence in plant tissues also suggests that these mycotoxins play a role in the pathogenesis of *Fusarium* on plants. This implies that mycotoxins play a role in disease and, therefore, reducing their toxicity to the plant may also prevent or reduce disease in the plant. Further, reduction in disease levels may have the additional benefit of reducing mycotoxin contamination on the plant and particularly in grain where the plant is a cereal plant.

There is a need, therefore, to decrease the contamination by mycotoxins of plants and, in particular, harvested goods.

Surprisingly, it has now been discovered that the treatment of plant propagation material, in particular the seed of a plant, with a chemical fungicide can reduce mycotoxin contamination in the plant and of harvested goods, such as the ears of cereals such as wheat or maize. This effect is unexpected due to the temporal separation between application of the treatment and formation of the ears: the fungicide used in the treatment will have long disappeared when the ears are formed.

Accordingly, the present invention provides a method of reducing mycotoxin contamination of a plant and/or harvested plant material, said method comprising
  a) treating plant propagation material with one or more chemical fungicides,
  b) germinating or growing said plant propagation material to produce a plant, and
  c) harvesting plant material from said plant.

A particular advantage of the invention is that by controlling pathogenic fungi, such as one or more *Fusarium* species, in early stages of a plant development mycotoxin contamination of the plant and/or plant harvested material produced from such fungi is controlled. In an embodiment, by controlling pathogenic fungi, such as one or more *Fusarium* species, infestation of the plant propagation material, the mycotoxin contamination in the plant or harvested plant material is reduced.

In an aspect, the present invention is a method comprising
  (i) treating plant propagation material with one or more chemical fungicides,
  (ii) germinating or growing said plant propagation material to produce a plant,
  (iii) harvesting plant material from said plant, and
  (iv) achieving a reduction in the mycotoxin contamination of (a) the plant grown from the treated plant propagation material and/or (b) harvested plant material.

The term "plant propagation material" is understood to denote all the generative parts of the plant, such as seeds, which can be used for the multiplication of the plant and vegetative plant material such as cuttings and tubers (for example, potatoes). There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may also be protected before transplantation by a total or partial treatment by immersion of the plant propagation material. In a preferred embodiment, the plant propagation material is a seed.

The fungicide or fungicides to be used in the treatment methods of the present invention include, but are not limited to, fludioxonil, difenoconazole, thiabendazole, triticonzole, ipconazole, prothioconazole, prochloraz, carbendazim, thiram, oxpoconazole, triflumizole, pefurazoate, metconazole, fluoxastrobin, azoxystrobin, pyraclostrobin, trifloxystrobin, picoxystrobin, guazatine, tebuconazole, tetraconazole, imazalil, epoxiconzole, carboxin, and fluquinconazole.

In a particular embodiment, the fungicide is fludioxonil, difenoconazole, thiabendazole, triticonzole, ipconazole, prothioconazole, prochloraz, carbendazim, thiram, oxpoconazole, triflumizole, metconazole, fluoxastrobin, azoxystrobin, trifloxystrobin, or tebuconazole; preferably fludioxonil or thiabendazole.

The method of the present invention is suitable for reducing mycotoxin contamination of a plant and/or harvested plant material of a number of useful crops including, but not limited to cereals (wheat, barley, rye, oats, maize (or corn), rice, sorghum and related crops), leguminous plants (beans, lentils, peas, soybeans, peanuts and related crops), oil plants (rape, mustard, sunflowers and related plants), cucumber plants (marrows, cucumbers, melons and related plants), vegetables (spinach, lettuce, asparagus, cabbages, carrots, eggplants, onions, pepper, tomatoes, potatoes, paprika and related plants). Harvested plant material obtained from plants treated using the method of the invention will have less mycotoxin contamination than harvested plant material from untreated plants. In an embodiment, the crop is one producing a product for human consumption, such as small grain cereals, maize, oats, and peanuts; preferably the crop is selected from maize and wheat.

In a particular embodiment of the invention, plant or harvested plant material has at least 10% less mycotoxin, more preferable at least 20% less mycotoxin, more preferably at least 30% less mycotoxin, more preferably at least 40% less mycotoxin, more preferably at least 50% less mycotoxin, more preferably at least 60% less mycotoxin, more preferably at least 70% less mycotoxin and more preferably at least 80% less mycotoxin contamination than harvested plant material from untreated plants.

The plant propagation material treatment with the defined fungicides of the invention preferably provide a reduction of between 20 to 60, more preferably between 30 to 50; %, in mycotoxin compared to treatments by other fungicides.

In the context of the present invention, harvested plant material may include, but is not limited to, cells, seeds, fruits, leaves, flowers, stems and the like. In a particular embodiment of the invention, the harvested plant material is seed.

Treatment of the plant propagation material can also involve treatment with further active compounds in combination with the chemical fungicides of the present invention, which treatment may be applied together and/or sequentially. These further compounds can be other pesticidal active ingredients, biological agents, fertilizers or micronutrient donors or other preparations that influence plant growth, such as inoculants. For example, seed is customarily treated with a protectant coating comprising insecticides, fungicides, bactericides, nematicides, molluscicides, bird repellents, growth regulators or mixtures thereof.

A single pesticidal active ingredient may have activity in more than area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity, and thiabendazole and captan can provide nematicide and fungicide activity.

In a particular embodiment, the fungicide of the invention is used in combination with one or more of further active compounds, such as insecticides, fungicides, bactericides, nematicides, molluscicides, bird repellents, growth regulators or mixtures thereof. Preferred to combination partners include clothianidin, imidacloprid, mefenoxam, metalaxyl, thiamethoxam, tefluthrin, abamectin and a bird repellent. A particularly effective treatment for maize is a combination comprising thiabendazole, fludioxonil, mefenoxam and azoxystrobin, and for wheat is a combination comprising fludioxonil.

The rates of application (use) of the pesticide(s) vary, for example, according to type of crop, the specific active ingredients in the combination, type of plant propagation material (if appropriate), but is such that the active ingredients in the combination is an effective amount to provide the desired enhanced action and can be determined by trials.

Generally for seed treatment, application rates can vary from 0.5 to 1000 g of active ingredient per 100 kg of seeds.

Advantageous rates of application of a fungicide are generally from 0.5 g to 500 g, preferably from 1 g to 100 g, or from 2.5 g to 25 g a.i. per 100 kg of plant seed. In an embodiment, fludioxonil can be applied at rate of 2.5 to 5 and thiabendazole at a rate of 10 to 20, each based on grams of a.i. per 100 kg of plant seed.

In the event the combination comprises (I) thiabendazole, (II) mefenoxam and (III) fludioxonil and azoxystrobin, typical application rates for seed treatment, in particular on corn, is 15-25 g of thiabendazole, 1-4 g of mefenoxam, 1-5 g of fludioxonil and 0.5-2 g of azoxystrobin, each on g/100 kg of seeds basis.

In a further aspect, the present invention provides for the use of a composition comprising one or more chemical fungicides to reduce mycotoxin contamination of a plant and/or harvested plant material wherein said composition is used to treat plant propagation material and said plant propagation material is germinated or grown to produce a plant from which said plant material is harvested.

In another aspect, the present provides the use of a plant propagation material treatment with one or more chemical fungicides to reduce mycotoxin contamination of a plant and/or harvested plant material.

Methods for applying or treating pesticidal active ingredients, mixtures and compositions thereof on to plant propagation material, especially seeds, are known in the art, and include dressing, coating, pelleting and soaking application methods of the propagation material. In a preferred embodiment, the combination is applied or treated on to the plant propagation material by a method such that the germination is not induced; generally seed soaking induces germination because the moisture content of the resulting seed is too high. Accordingly, examples of suitable methods for applying (or treating) a plant propagation material, such as a seed, is seed dressing, seed coating or seed pelleting and alike.

It is preferred that the plant propagation material is a seed. Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed, according to techniques understood by a skilled person, either before or after the treatment.

Even distribution of the active ingredients and adherence thereof to the seeds is desired during propagation material treatment. Treatment could vary from a thin film (dressing) of the formulation containing the active ingredient(s) on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the combination. In particular, seed coating or seed pelleting are preferred in treatments according to the invention. As a result of the treatment, the active ingredients are adhered on to the seed and therefore available for pathogenic and/or pest control.

The treated seeds can be stored, handled, sowed and tilled in the same manner as any other active ingredient treated seed.

The pesticides (including fungicides) may be used in unmodified form but is normally used in the form of compositions. It can be applied together with further carriers, surfactants or other application-promoting adjuvants customarily employed in formulation technology. Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

The pesticide is conveniently formulated in known manner e.g. into emulsifiable concentrates, suspension concentrates, coatable pastes, directly sprayable or dilutable solutions, dilute emulsions, wettable powders, soluble powders, flowable suspensions dusts, granules, or by encapsulation in e.g. polymer substances. As with the nature of the compositions, the methods of application, such as spraying, atomising, dusting, scattering, coating or pouring, are chosen in accordance with the intended objectives and the prevailing circumstances.

The formulations are prepared by any manner known in the art, e.g. by homogeneously mixing and/or grinding the active ingredients with extenders, e.g. solvents, solid carriers and, where appropriate, surface-active compounds (surfactants).

Suitable solvents include, but are not limited to: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice; broken brick, sepiolite or bentonite, and suitable nonabsorbent carriers are, for example, calcite or sand. In addition, a great number of pregranulated materials of inorganic or organic nature can be used, e.g. especially dolomite or pulverised plant residues.

Depending upon the nature of the active ingredient to be formulated, suitable surface-active compounds are non-ionic, cationic and/or anionic surfactants having good emulsifying, dispersing and wetting properties. The term 'surfactants' will also be understood as comprising mixtures of surfactants. The surfactants customarily employed in formulation technology are well known in the art.

Particularly advantageous application-promoting adjuvants are also natural or synthetic phospholipids of the cephalin and lecithin series, e.g. phosphatidylethanolamine, phosphatidylserine, phosphatidylglycerol and lysolecithin.

When the fungicide is used in combination with further ingredients, such as other pesticides, the components can be applied to the plant propagation material to be treated either simultaneously or in succession at short interval, for example on the same day, if desired together with further carriers, surfactants or other application-promoting adjuvants customarily employed in formulation technology. In a preferred embodiment, the components are applied simultaneously.

In the event that the components are applied simultaneously, they may be applied as a composition containing each of the components, in which case each of the components can be obtained from a separate source and mixed together (known as a tank-mix, ready-to-apply, spray broth or slurry), optionally with other pesticides, or the components can be obtained as a single mixture source (known as a pre-mix, concentrate, formulated compound (or product)), and optionally mixed together with other pesticides.

Normally, a tank-mix formulation for seed treatment application comprises 0.25 to 80%, especially 1 to 75%, active ingredient compounds, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, active ingredient compounds, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

Conventional technologies for controlling mycotoxins, such as foliar spray of fungicides and use of biological agents, may also be used in combination with the present invention.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The following Examples are given by way of illustration and not by way of limitation of the invention.

EXAMPLES

Winter wheat seeds are dipped in a macroconidia suspension of GFP genetically modified strain of F. graminearum at $10^4$ spores/mL.

A sample of the inoculated seeds is treated with fludioxonil at a rate of 5 grams of active ingredient per 100 kg of seeds (designated as lot B).

The untreated inoculated seeds (lot A) and fludioxonil treated inoculated seeds (lot B) are grown in pots until full maturity (earing).

The detection of the *Fusarium* at different stages of the plant development is carried out using polymerase chain reaction (PCR) technology in order to specifically detect the *Fusarium* species.

From the beginning till the full maturity of the plant, segments of the stem were cut to detect by PCR the presence of *Fusarium*.

At full maturity of the plant, the grain is harvested and the DON level is quantified in both the untreated or fludioxonil treated seeds. The results are summarized in the tables 1 and 2.

TABLE 1

Detection in wheat of modified *Fusarium graminearum* at different growth stages

| Growth stage of plant at PCR analysis (BBCH GS) | Segments | Intensity of *F. graminearum* (PCR analysis: 0 to 4 scale)* | |
|---|---|---|---|
| | | Lot A untreated seed | Lot B treated seed |
| End of tillering (GS 29) | primary roots | 0 | 0 |
| | rhizome | 4 | 0 |
| | Secondary roots | 0 | 0 |
| | Bottom of the plant (0.5 cm) | 2 | 0 |
| | Above bottom of the plant (0.5 cm) | 1 | 0 |
| Ear 1-2 cm (GS 31) | First internode | 3 | 0 |
| | Second internode | 0 | 0 |
| | Future internodes and ear | 0 | 0 |
| Beginning of earing (GS 51) | $1^{st}$ internode | 4 | 0 |
| | $2^{nd}$ internode | 1 | 0 |
| | $3^{rd}$ internode | 0 | 0 |
| | $4^{th}$ internode | 0 | 0 |
| | ear | 0 | 0 |
| Full maturity (GS 94) | $1^{st}$ internode | 4 | 0 |
| | $2^{nd}$ internode | 4 | 0 |
| | $3^{rd}$ internode | 3 | 0 |
| | $4^{th}$ internode | 3 | 0 |
| | $5^{th}$ internode | 2 | 0 |
| | Ear + grains | 2.5 | 0 |

*3 replicates of 6 plants are analysed; the intensity of the amplification product was evaluated with a 0 to 4 scale: 0 = no band - 0.5 = very weak intensity band - 1 = weak intensity band - 2 = medium intensity band - 3 = important intensity band - 4 = very important intensity band.

TABLE 2 deoxynivalenol amount (DON in ppb) in the ear of wheat

| Growth stage of analysis (BBCH) | Segments | Amount of DON (ppb)* | |
|---|---|---|---|
| | | Lot A untreated seed | Lot B treated seed |
| Full maturity (GS 94) | Ear + grains | 7650 ppb | 0 |

*3 replicates of 6 plants are analysed.

The invention claimed is:

1. A method of reducing mycotoxin contamination of a plant and/or harvested plant material, said method comprising:
   a) treating plant propagation material with a composition comprising fludioxonil,
   b) germinating or growing said plant propagation material to produce a plant, and
   c) harvesting plant material from said plant
      wherein the plant propagation material, the plant, and the harvested plant material have at least 20% reduction of mycotoxin as compared to an untreated plant propagation material.

2. The method according to claim 1 wherein the mycotoxin contamination is caused by fungi infestation of the plant propagation material.

3. The method according to claim 1 wherein the mycotoxin is one or more of a fumonisin and a trichothecene.

4. The method according to claim 1 wherein the mycotoxin is deoxynivalenol and/or zearalenon.

5. The method according to claim 1, wherein the composition further comprises a fungicide selected from the group consisting of difenoconazole, thiabendazole, ipconazole, prothioconazole, triticonzole, prochloraz, carbendazim, thiram, oxpoconazole, triflumizole, pefurazoate, metconazole, fluoxastrobin, azoxystrobin, pyraclostrobin, trifloxystrobin, picoxystrobin, guazatine, tebuconazole, tetraconazole, imazalil, epoxiconzole, carboxin, fluquinconazole, and mixtures thereof.

6. The method according to claim 5, wherein the composition further comprises a fungicide selected from the group consisting of difenoconazole, thiabendazole, ipconazole, prothioconazole, triticonzole, prochloraz, carbendazim, thiram, oxpoconazole, triflumizole, metconazole, fluoxastrobin, azoxystrobin, trifloxystrobin, tebuconazole, and mixtures thereof.

7. The method according to claim 1 wherein the plant propagation material is a seed.

8. The method according to claim 7 wherein the seed is a cereal seed.

9. The method according to claim 8, wherein the cereal seed is a wheat, barley, rye, oats, maize, rice or sorghum seed.

10. The method according to claim 1, wherein the harvested plant material is seed.

11. The method of claim 1, wherein the plant propagation material is further treated with insecticides, fungicides, bactericides, nematicides, molluscicides, bird repellents, growth regulators, biological agents, fertilizers, micronutrient donors, or mixtures thereof.

12. The method of claim 1, wherein the plant propagation material, plant and the harvested plant material have at least 50% reduction of mycotoxin as compared to an untreated plant propagation material.

13. The method of claim 1, wherein the plant propagation material, plant and the harvested plant material have at least 60% reduction of mycotoxin as compared to an untreated plant propagation material.

* * * * *